United States Patent
Spaziante et al.

(10) Patent No.: US 9,793,560 B2
(45) Date of Patent: Oct. 17, 2017

(54) ESTIMATION OF THE STATE OF CHARGE OF A POSITIVE ELECTROLYTE SOLUTION OF A WORKING REDOX FLOW BATTERY CELL WITHOUT USING ANY REFERENCE ELECTRODE

(71) Applicant: Hydraredox Technologies Holdings Ltd., Wirral (GB)

(72) Inventors: Placido Maria Spaziante, Bangkok (TH); Michael Dichand, Nussdorf (AT)

(73) Assignee: HYDRAREDOX TECHNOLOGIES HOLDINGS LTD., Wirral (GB)

( * ) Notice: Subject to any disclaimer, the term of this patent is extended or adjusted under 35 U.S.C. 154(b) by 76 days.

(21) Appl. No.: 14/890,943

(22) PCT Filed: May 16, 2013

(86) PCT No.: PCT/IB2013/054005
§ 371 (c)(1),
(2) Date: Nov. 13, 2015

(87) PCT Pub. No.: WO2014/184617
PCT Pub. Date: Nov. 20, 2014

(65) Prior Publication Data
US 2016/0111740 A1    Apr. 21, 2016

(51) Int. Cl.
*G01R 31/36* (2006.01)
*H01M 8/0444* (2016.01)
(Continued)

(52) U.S. Cl.
CPC .... *H01M 8/04477* (2013.01); *G01R 31/3634* (2013.01); *G01R 31/3651* (2013.01);
(Continued)

(58) Field of Classification Search
CPC ............. G01R 31/36; G01R 31/3606; G01R 31/3637; G01N 27/403; G01N 27/416
See application file for complete search history.

(56) References Cited

FOREIGN PATENT DOCUMENTS

WO    2012135473 A2    10/2012

OTHER PUBLICATIONS

Kim et al., "Investigation of Voltage Loss in Vanadium Redox Flow Battery," Abstract #184, 218th ECS Meeting, 2010 The Electrochemical Society.*

(Continued)

*Primary Examiner* — Alexander Noguerola
(74) *Attorney, Agent, or Firm* — Lucas & Mercanti, LLP

(57) ABSTRACT

A Method and device for measurement is disclosed in operation, an undivided cell sensor immersed at any desirable point of the positive electrolyte circuit is constantly supplied at a controlled fixed DC bias voltage between the positive metal electrode and the porous carbon counter-electrode by an appropriate voltage regulator of adequate power capability, or cyclically at two or more different voltages, all within a range that includes the region between 0.35V and 0.45V, measuring simultaneously the current flowing across the undivided cell sensor at the fixed voltage or voltages bias. By correlating the paired voltage and current values, using a look up table compiled at calibration, estimated values of the degree of oxidation or state of charge of the redox ion couple of the positive electrolyte solution are produced.

8 Claims, 7 Drawing Sheets

(51) Int. Cl.
    *H01M 8/18*    (2006.01)
    *H01M 8/20*    (2006.01)
    *G01N 27/403*  (2006.01)
(52) U.S. Cl.
    CPC ....... *H01M 8/04455* (2013.01); *H01M 8/188* (2013.01); *H01M 8/20* (2013.01); *G01N 27/403* (2013.01); *Y02E 60/528* (2013.01)

(56) References Cited

OTHER PUBLICATIONS

Ferrigno et al., "Membraneless Vanadium Redox Fuel Cell Using Laminar Flow," J. Am. Chem. Soc. 2002, 124, 12930-12931.*
Tang et al., "Monitoring the State of Charge of Operating Vanadium Redox Flow Batteries", ESC Transactions, 2012, vol. 41(23) pp. 1-9.
Mohamed et al., "Estimating the State-of-Charge of all-Vanadium Redox Flow Battery using a Divided, Open-circuit Potentiometric Cell", Electronics and Electrical Engineering, 2013, vol. 19(3) pp. 37-42.
Corcuera et al., "State-of-Charge Monitoring and Electrolyte Rebalancing Methods for the Vanadium Redox Flow Battery", Eur.Chem. Bull, 2012, vol. 1(12) pp. 511-519.
International Search Report and Written Opinion based on International Application No. PCT/IB2013/054005, Mailed Feb. 6, 2014 (9 pages).

* cited by examiner

ESTIMATION OF THE STATE OF CHARGE OF A POSITIVE ELECTROLYTE SOLUTION OF A WORKING REDOX FLOW BATTERY CELL WITHOUT USING ANY REFERENCE ELECTRODE

CROSS-REFERENCE TO RELATED APPLICATION

This application is a 371 of PCT/IB2013/054005, filed May 16, 2013.

BACKGROUND

Technical Field

This disclosure relates in general to redox flow battery (RFB) systems for energy storage, and in particular to the so-called all-vanadium RFB system. This disclosure addresses the problem of monitoring the state of charge of the positive electrolyte solution and of the negative electrolyte solution.

Related Art

RFB energy storage systems [1-7] are recognized as particularly efficient and flexible candidates for large scale energy storage requirements of intelligent power distribution networks being developed.

The all-vanadium (V/V) RFB system using the redox couples $V^{+2}/V^{+3}$ in the negative electrolyte solution and $V^{+4}/V^{+5}$ in the positive electrolyte solution is probably the one that has had significant industrial applications and that is most extensively studied. Other similar RFB systems like Fe/V, V/Br, Cr/Fe, Zn/Ce, Polysulfide/Br, have been studied but have not had a comparable commercial acceptance. A common feature to these systems is that, for economically acceptable current densities to be supported, porous and fluid permeable electrodes are necessary. Moreover, chemical inertness of the electrode materials that need to be retained when switching from cathodic polarization to anodic polarization during a cycle of charging and discharging of the redox storage system, and the requisite of having a relatively high $H^+$ discharge over-voltage when negatively polarized in respect to the electrolyte solution and a high OH discharge over-voltage when positively polarized in respect to the electrolyte solution, obliges to use carbon base electrodes.

Yet, preventing parasitic $OH^-$ discharge and/or $H^+$ discharge in case of localized depletion of oxidable and reducible vanadium ions of the respective redox couples in the two solutions because of non uniform mass transport and/or electrical potential throughout porous electrode felts of non woven activated carbon fibers, generally sandwiched between the ion permeable cell separating membrane and the surface of a conductive current distributing plate, remains a critical aspect.

Parasitic oxygen discharge at the carbon electrode may accidentally becomes the main current supporting anodic reaction if the design maximum current density limit is for some reasons surpassed or if the charging process is accidentally protracted beyond full vanadium oxidation in a positive electrolyte solution to $V^{+5}$. In the latter event, another serious effect may start to manifest itself, notably a gradual precipitation of vanadium pentoxide according to the reaction: $2VO_2^+ + H_2O = V_2O_5 + 2H^+$.

The first of these hazardous occurrences may lead to a rapid destruction of the carbon felt and of the carbon-based current collecting plates by nascent oxygen with generation of CO and $CO_2$. For this reason many substances have been identified as poisoning agents of oxygen evolution on carbon anodes in the typical sulphuric acid electrolyte solutions of vanadium RFBs like antimony ($Sb^{+3}$), Borax and tellurium ($Te^{+4}$), generally preferred because besides raising the oxygen evolution over-voltage, they also poisons $H^+$ discharge in case of migration/contamination of the negative electrolyte solution. The second occurrence, if unchecked, causes clogging most likely in the pores of the carbon felt electrode, which is particularly difficult to remedy, and unbalancing of the electrolytes. As it is well known, parasitic hydrogen evolution in a vanadium RFB energy storage cell may be favoured by accidental contamination of the electrolyte solutions with metals having a low hydrogen over-voltage like Fe, Ni, Co, . . . etc. that may deposit on the carbon electrode structure, and/or when $V^{+3}$ has been completely reduced to $V^{+2}$ in which case the only electrode reaction that may support circulation of electric current becomes the electrolysis of water.

Specific monitoring of working conditions in the cells is indispensable and its shortcomings has been the cause of costly failures. More sophisticated and reliable ways of controlling the operation of RFB energy storage systems are been developed.

Prior patent application No. PCT/IB2012/057342, of the same applicants, discloses a reliable monitoring system of the operation conditions that provides a long sought detectability at single cell level, impossible with the multi-cell bipolar stacks typical of known industrial all-vanadium flow redox batteries. The content of his prior patent application is herein incorporate by express reference.

The technique of monitoring the state of charge of the electrolyte solutions by measuring the open cell voltage (OCV) in a minuscule cell replica of the battery cells through which diverted streams of the positive and negative solutions flow as depicted in FIG. 1, or in a simplified though equivalent manner described in said prior application, is well known. However, what is measured is the "overall" state of charge and any intervened unbalance between the state of charge of the negative and positive electrolyte solutions remains undetected. Given that in all-vanadium RFB systems and mutatis-mutandis also in other RFB systems a perfect symmetrical reduction and oxidation of the redox ion couples respectively used in the negative and in the positive electrolyte solutions can hardly be retained over many charge/discharge cycles, the risk remains of running into critical limit conditions in one or the other of the two electrolyte solutions.

As widely accepted, in all-vanadium RFB systems the causes of unbalance are oxidation of reduced vanadium ions $V^{+2}$ by contact with ambient air in the tank and parasitic hydrogen evolution (gassing) occurring on the negative electrode. This progressively leads to a state of charge of the positive electrolyte solution exceeding the state of charge of the negative electrolyte solution. The opposite condition of unbalance cannot occur in practice.

An accumulated unbalance of charge between the two electrolyte solutions, the effect of which being that a measured OCV of magnitude short of the one expected at full charge may mask the fact that the positive electrolyte solution has reached a condition of full charge (all vanadium oxidized to $V^{+5}$) whilst the negative electrolyte solution has not yet reached a complete reduction of all vanadium to $V^{+2}$, but just a partial reduction in a $V^{+2.4}$–$V^{+2.6}$ range. This normally occurs when periodically re-mixing the two electrolyte solutions for re-establishing a volumetric and/or constituents balance of the two solutions, as it is generally practiced (easier than adjustments by other ways). This mechanism, besides progressively reducing the storage capacity really available, poses serious risks of damaging the positive carbon felt electrodes of the cells because of a concurrent/substitute oxygen discharge through electrolysis of the water solvent.

There is an evident need of monitoring the state of charge of the single electrolyte solution that in the case of an all-vanadium RFB system point to the positive electrolyte solution as the critical one to be monitored. This requires the use of standard reference electrodes. Proposed alternatives to the use of expensive and bulky instruments like a standard hydrogen electrode, have not sorted satisfactory results in terms of precision and reliability.

SUMMARY OF THE DISCLOSURE

A precise and reliable method of producing a measure of the state of charge of the positive electrolyte solution of a working redox flow battery without using a reference electrode has been found and is the object of this disclosure.

In the work that led to devise the method of this disclosure, the applicants have studied the voltage-current characteristic curves of an undivided cell assembly comprising a stable electro catalytic metal electrode and a porous carbon base counter-electrode that may be similar to the porous carbon base electrodes employed in the battery cell or even different from it, immersed in the positive electrolyte solution of an all vanadium battery, for different degrees of oxidation of the vanadium from $V^{+3.5}$ to $V^{+5}$. In a region of the voltage-current Cartesian plane of a DC voltage bias of the supplied cell assembly insufficient to sustain oxygen evolution on the positively biased metal electrode, the applicants noticed a cross-over region that preceded a region of convergence toward a common minimum voltage of about 0.8 mV as the current decreases to nil. In this region of convergence, the characteristics curves for different states of charge of the solution undergo a distinctive bulging the amplitude of which appeared in first approximation proportional to the degree of oxidation or in other words to the state of charge of the positive electrolyte solution.

By the expression stable electro catalytic metal electrode it is intended a commercial dimensionally stable anode (DSA®) compatible to discharge oxygen without degradation of its electro catalytic properties. Typically, a titanium base electrode having a ceramic coating of oxides belonging to the group of Ta, Sn, Zr, Ir, Hf and Rh, is particularly suited to discharge oxygen with a relatively low over-voltage (i.e. it is electro catalytic) for repeated periods of time without losing its properties.

Ideally, for a balanced state of charge of the two electrolyte solutions, the open circuit voltage (OCV) commonly measured on a dedicated scaled test cell replica of a battery cell, is the sum of the modulus of the state of charge of the negative electrolyte solution and of the state of charge of the positive electrolyte solution, less several voltage drop contributions that are generally all tied to the current flowing through the cell and because of that become substantially negligible at the very low current levels of the spread out region of distinctive bulging of the characteristic curves of the different solutions.

Considering the likelihood of a progressive unbalancing of the state of charge between the two electrolytes circulating in the respective flow compartments of the battery cells, as already remarked, in an all-vanadium RFB system and alike systems, risks of recurrent accidental overcharges of the positive electrolyte solution and attendant damages of the positive carbon felt electrodes could be effectively prevented only by directly monitoring its degree of oxidation (state of charge) for generating an alert signal when the degree of oxidation of the redox ion couple or state of charge surpasses a given threshold.

In the interval between about 0.35V and 0.45V, such a spread out of the voltage-current characteristic curves is at maximum of amplitude and allows an excellent discrimination of the state of oxidation of vanadium by locating the point on the voltage-current plane, on which the characteristic curves at different known degrees of oxidation have been recorded during a calibration work carried out on the specific undivided cell sensor to be used thereafter for monitoring the state of charge of the positive electrolyte solution.

In operation, the undivided cell sensor that may be immersed at any desirable point of the positive electrolyte circuit, may be constantly supplied at a controlled fixed DC bias voltage between the positive metal electrode and the porous carbon counter-electrode by an appropriate voltage regulator of adequate power capability, or cyclically at two or more different voltages, all within a range that includes the region between 0.35V and 0.45V, measuring simultaneously the current flowing across the undivided cell sensor at the fixed voltage or voltages bias.

Alternatively, in consideration of the relatively slow change of the degree of oxidation of the vanadium redox couples contained in the circulating electrolyte solutions, compared with the practically instantaneous reading of a pair of voltage-current values, the measurements, whether at a single bias voltage or cyclically at a number of different bias voltages, may be carried out at intervals of time of minutes or tens of minutes or even longer, with the advantage of a perfect refreshing of the solution wetting the surface of the electrodes, in particular of the porous carbon electrode, because of the streaming electrolyte solution or by diffusive equalization in case the sensor be immersed in a substantially static pool of the solution.

According to another possible embodiment, execution of the measurements, whether at a single bias voltage or cyclically at a number of different bias voltages, may even be triggered when the monitored OCV surpasses a set threshold of about 1.344V (that in case of perfect balance between the two electrolyte solutions would correspond to a degree of oxidation of $V^{+4.45}$ in the positive electrolyte solution), in order to monitor thereafter any further charging and eventually alert when a safe limit threshold is reached, meaning that the vanadium has been oxidized to a degree of oxidation of vanadium close to the limit $V^{+5}$ (at which the OCV would reach about 1.576V, in case of a perfectly balanced system). This range coincides with the critical "end of charge process" of the positive electrolyte solution that practically poses the maximum concerns to the operators of vanadium RFB systems for the reasons discussed in the introductory part of this description.

Signal conditioning, A/D conversion, digital data acquisition, temporary data storage and data processing for correlating the measured voltage-current data pairs to the correspondent degree of oxidation or state of charge of the positive electrolyte solution to be output may be suitable implements for real time estimated degree of oxidation or state of charge of the positive electrolyte solution starting from the voltage-current pair or pairs of measured values using the undivided cell sensor according to an embodiment of the novel method of this disclosure.

DETAILED DESCRIPTION OF EMBODIMENTS

Figure 1:
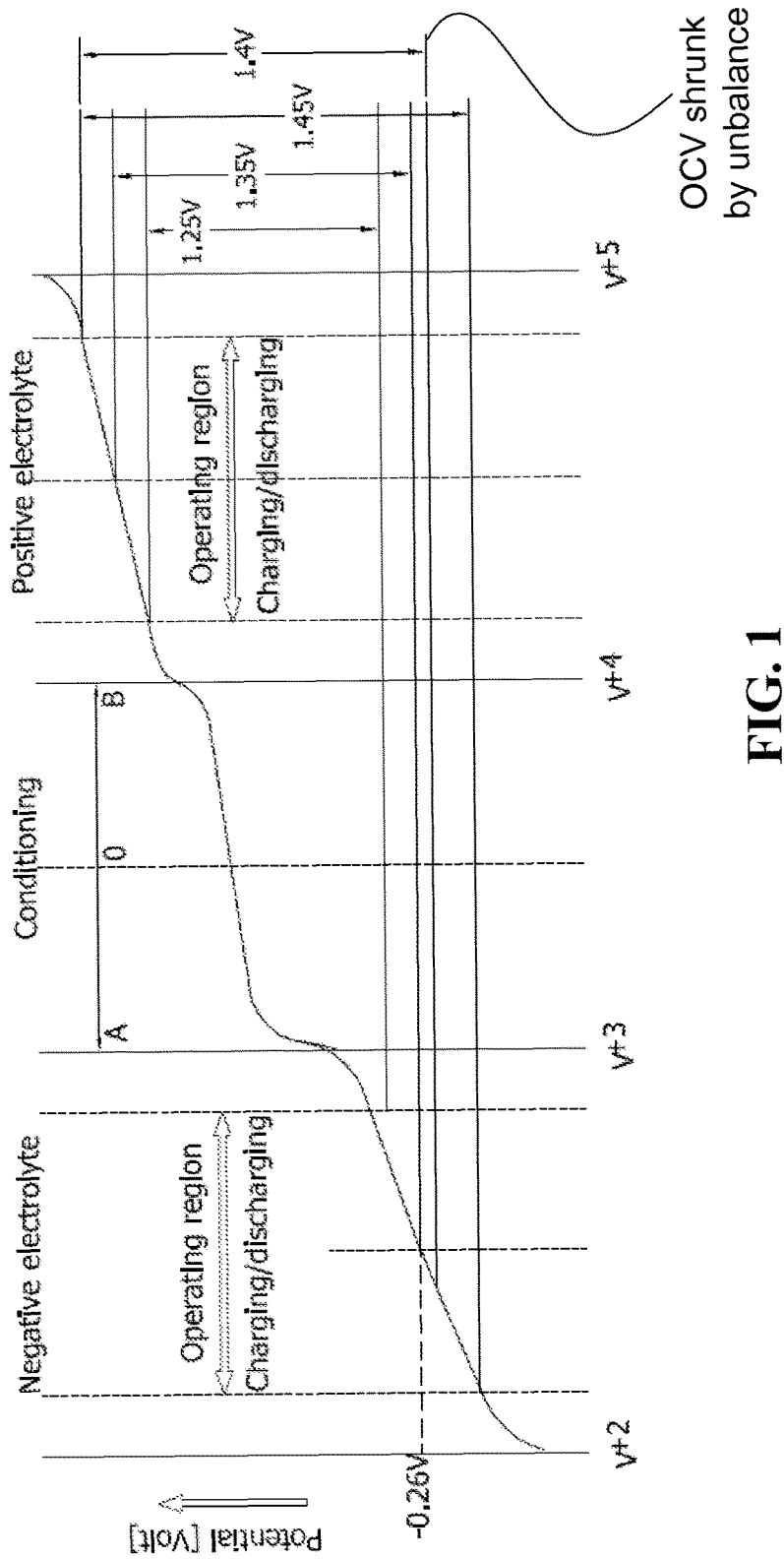
FIG. 1 is a diagram showing the electrochemical potential characteristic curve and the open circuit cell voltage for the distinct phases of charging and discharging of a vanadium RFB system.

A diagram showing the electrochemical potential characteristic curve and the open circuit cell voltages for the distinct phases of charging and discharging of an all-vanadium RFB system is depicted in FIG. 1. Typically, operators concern focuses on preventing conditions of oxidation of vanadium ions in the positive electrolyte solution to a degree such to cause a starvation of $VO^{2+}$ ions at the wetted surface of the positive porous carbon electrodes of the battery cells to be oxidized to $VO_2^+$. This, in practice means that a safety maximum limit of about 1.45-1.50V of the OCV value is generally considered a viable full charge condition of the RFB system. However, any undetected unbalance of the respective states of charge of the negative and positive solutions, because of a progressive oxidation of the negative electrolyte solution by exposure to air and/or parasitic hydrogen evolution (gassing) phenomena at the negative porous carbon electrodes when functioning at elevated current densities, may shrink at its negative end the OCV to a point that even a would-be-safe 1.45V reading may be masking a condition of excessive oxidation degree of the vanadium ions in the positive electrolyte solution, as it may be assessed only on the basis of the OCV information. The arrows span of such a one-ended shrunk OCV traced on the diagram of FIG. 1 shows the baffling shift to which the OCV information is subjected because of the contraction at its negative end of the OCV magnitude in case of charge unbalance between the two solutions.

Figure 2:
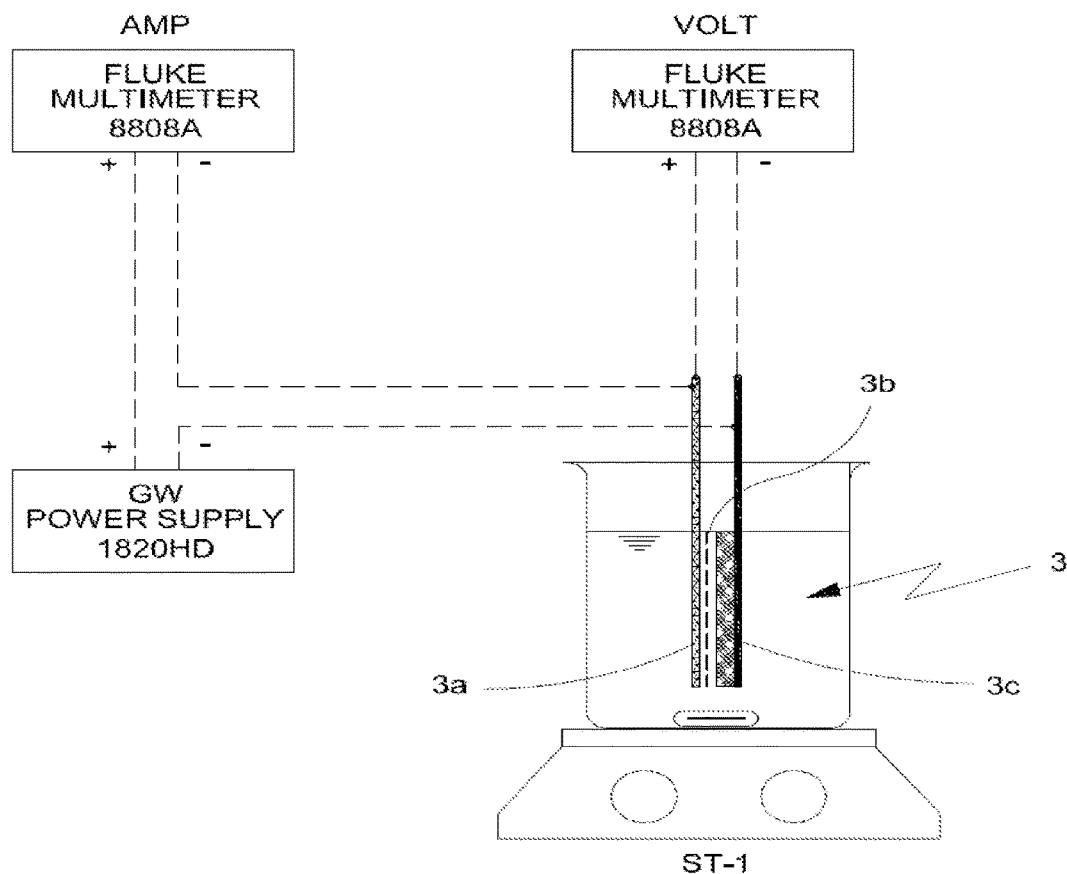
FIG. 2 shows the laboratory set-up used for studying the electrochemical behaviour of a charged positive electrolyte solution of a vanadium RFB subjected to electrolysis in a undivided cell having a stable electro catalytic metal anode and a porous carbon cathode.

FIG. 2 shows the laboratory set-up used for studying the electrochemical behaviour of a charged positive electrolyte solution of a vanadium RFB subjected to electrolysis in a undivided cell 3 having a stable electro catalytic metal anode 3a and a porous carbon cathode 4c. A fluid permeable plastic insulating screen 3b prevents a short circuiting contact between the opposed electrodes. The immersed portion of the electrode assembly had a projected cell area of 18 cm².

The metal anode 3a was an expanded titanium plate with a void/solid ratio of about 0.4, coated with a electro catalytic ceramic coating of oxides of tantalum, zirconium, tin and iridium conferring to the anode the ability to discharge oxygen without losing in time its electro catalytic property.

The porous carbon cathode 3c consisted in a compressed bed of active carbon particles contacted by a graphite back plate, connectable to the negative terminal of a controlled power supply.

When powering the test cell at a certain output voltage of the power supply Vout, the voltage drop contributions are $$V\text{out} = E_p - E_n + \eta_n + \eta_p + \eta_c + R\,I\text{cell} \quad (1)$$

$E_p$ is the positive electrode potential versus the electrolyte solution that is required for the following possible reactions to occur at the anode 3a:

a) oxidation of V+4 to V+5 according to the reaction:

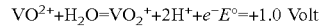

In fact, this reaction requires a potential of +1.0 Volt (at standard conditions) and slightly higher or lower if the conditions are not standard (in standard conditions the concentration of $VO_2^+$ is identical to the concentration of $VO^{2+}$).

This reaction will occur only if V+4 (i.e. $VO^{2+}$) is present and cannot occur any longer if the state of oxidation of the electrolyte is +5.0.

b) evolution of oxygen according to the reaction:

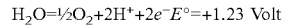

$E_n$ is the negative electrode potential that is generated by the following reaction of those theoretically possible at the carbon cathode 3c:

a) reduction of V+5 to V+4: $VO_2^+ + 2H^+ + e^- = VO^{2+} + H_2O$ $E° = +1.0$ Volt This reaction generates a potential of +1.0 Volt (at standard conditions) and slightly higher or lower if the conditions are not standard (in standard conditions the concentration of $VO_2^+$ is identical to the concentration of $VO^{2+}$). Conventionally we attribute a positive sign to this potential because of the sign "minus" used in equation (1).

b) the other possible reaction of hydrogen discharge: $2H^+ 2e^- = H_2O$ $E° = +0.0$ Volt, does not occur because the porous carbon cathode (free of metal contaminants) used in the test cells has a high over-voltage for hydrogen ion discharge.

$\eta_n$ is the negative electrode over-potential for the sustained electrode reaction specified above, $\eta_p$ is the positive electrode over-potential for the sustained electrode reaction specified above, $\eta_c$ is the concentration over-potential These over-potentials (factors of irreversibility of the charge-discharge process) are all a logarithmic function of the current i flowing through the test cell according to the well known Tafel equation.

R is the internal resistance of the test cell.

Therefore, equation (1) can be written as:

$$V_{out} = E_p - E_n + \alpha_n \ln i + \beta_p \ln i + \gamma_c \ln i + Ri \quad (1)$$

In this equation $E_p$ and $E_n$ are the only terms that are not a function of the current "i". If the test cell is driven at voltages capable of forcing a relatively high current, the terms that are function of "i" become predominant and much larger than $E_p$ and $E_n$. By contrast, if the test cell is driven at relatively low voltages a condition may be reached at which the cell current becomes very low, rendering the terms other than $E_p$ and $E_n$ practically negligible. The equilibrium equation (1) becomes:

$$V_{out} = E_p - E_n.$$

Figure 3:
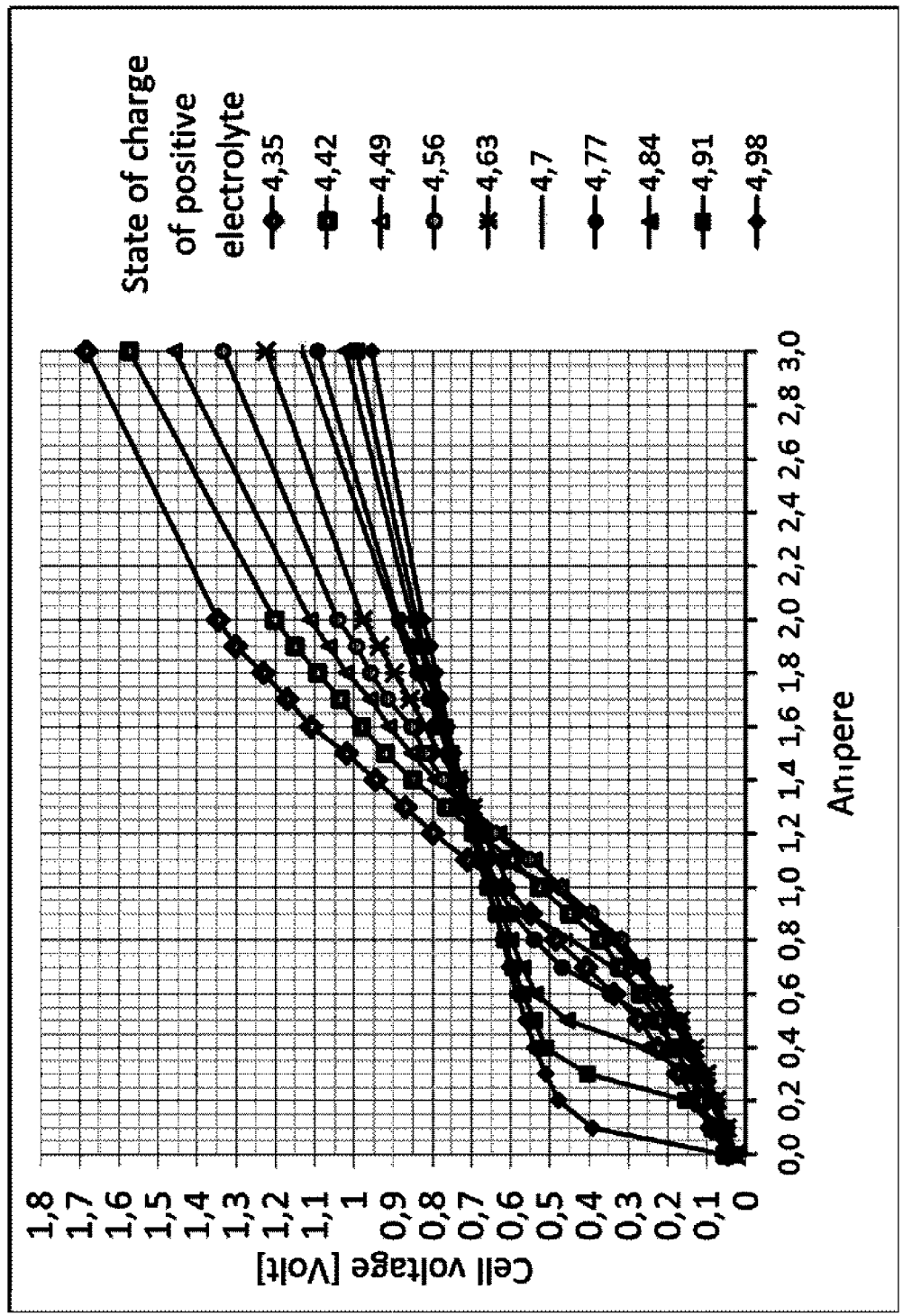
FIG. 3 shows broad-range voltage-current characteristics curves obtained in laboratory for positively charged vanadium electrolyte solutions of different known degrees of oxidation, forcing a current varying from 0 to 4.0 A through a test cell of about 18 cm².

FIG. 3 shows broad-range voltage-current characteristics curves obtained with the set up of FIGS. 2a and 2b for positively charged vanadium electrolyte solutions of different known degrees of oxidation, forcing a current varying from 0 to 4.0 A through the test cell of about 18 cm². It is evident a cross-over region at currents of 0.7 A-0.8 A preceding a region of convergence toward a voltage of about 0.8 mV when the current has become null, wherein the characteristics curves for different states of charge undergo a bulging of amplitude proportional to the degree of oxidation in other words to the state of charge of the positive electrolyte solution. In the interval between about 0.35V and 0.45V, such a spread out of the voltage-current characteristic curves is at maximum of amplitude and allows an excellent discrimination of the state of oxidation of vanadium by locating the point on the voltage-current plane.

Figure 4:
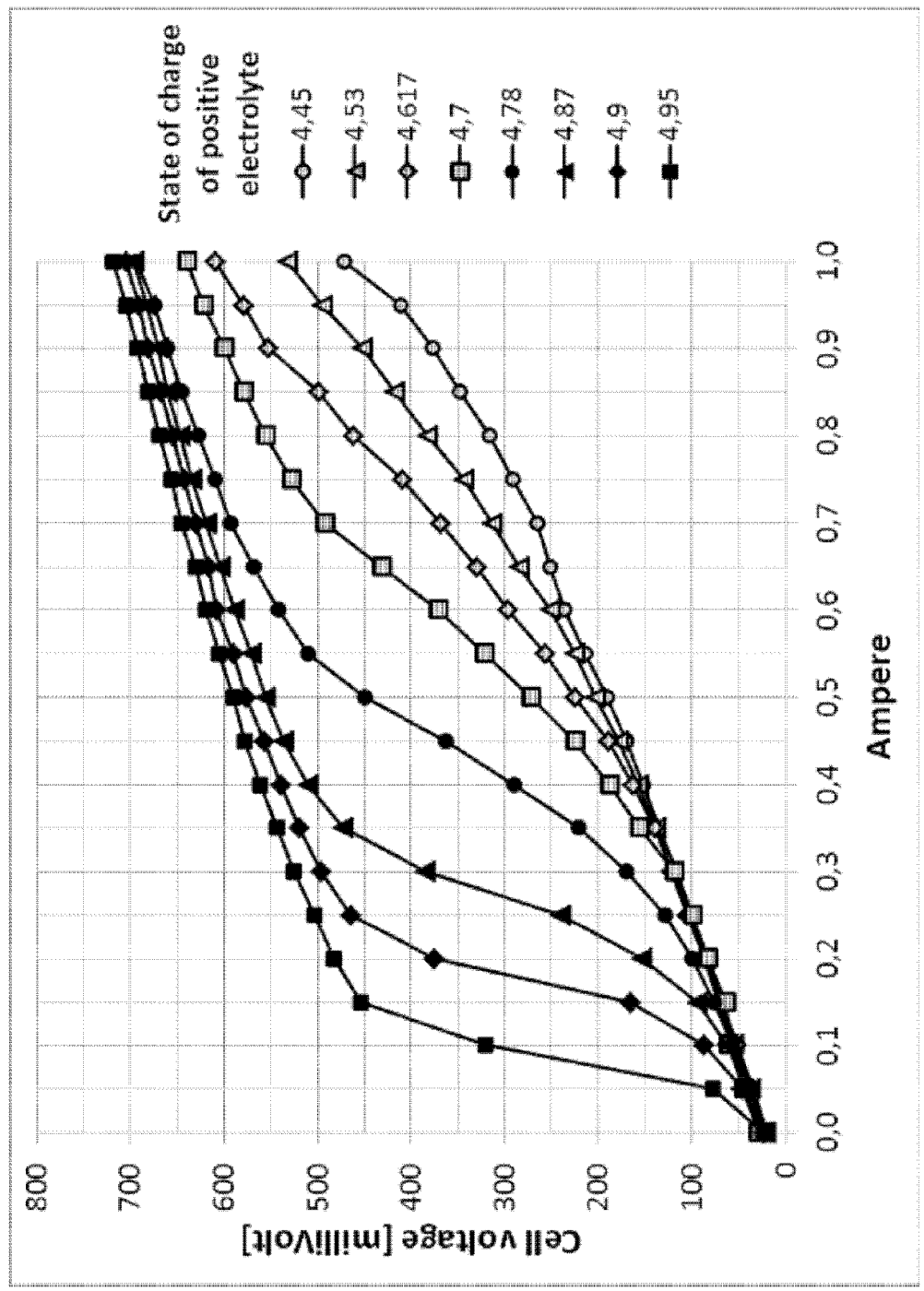
FIG. 4 shows voltage-current characteristics curves obtained in laboratory with the test cell for positively charged vanadium electrolyte solutions of different known degrees of oxidation, expressed in terms of correspondent OCV values of a balanced RFB, in the region below an applied voltage of about 0.7V to the cell voltage.

FIG. 4 shows voltage-current characteristics curves obtained in laboratory with the test cell for positively charged vanadium electrolyte solutions of different known degrees of oxidation, expressed in terms of correspondent OCV values of a balanced RFB, in the region of convergence beginning below an applied voltage of about 0.7 V to the cell voltage. In this region of distinct spreading out by a peculiar bulging that is more and more pronounced for an increasingly charged state of the positive electrolyte solution, the characteristic curves at different known degrees of oxidation, expressed in terms of correspondent OCV values of a balanced RFB, have been recorded during a calibration work carried out on the specific undivided test cell, that may really be defined an oxidation state sensor.

Figure 5:
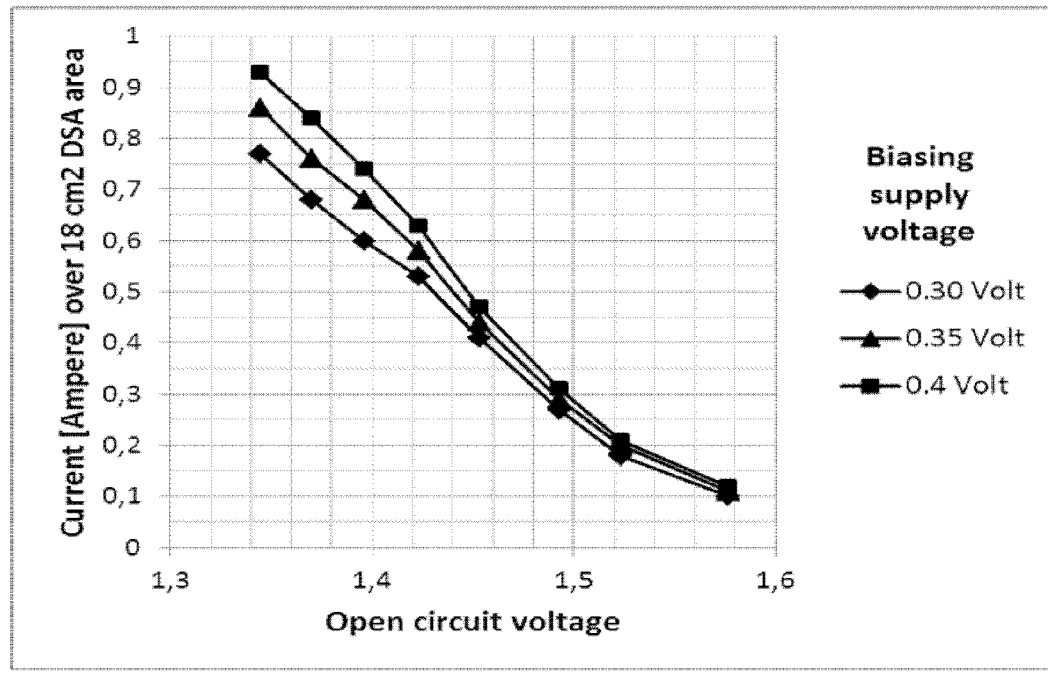
FIG. 5 shows the characteristics curves in the Cartesian plane of the current measured at the indicated three different bias voltages applied to the test cell and the known state of charge of the vanadium redox couple in the positively charged electrolyte solutions used for the tests.

Having expressed in terms of correspondent OCV values of a balanced RFB the known state of charge of the solutions used for calibrating the sensor, FIG. 5 shows the correlation characteristics in a Cartesian plane of the current measured at the indicated three different bias voltages applied to the test cell (sensor) and the known state of charge of the vanadium redox couple in the positively charged electrolyte solutions used.

Figure 6:
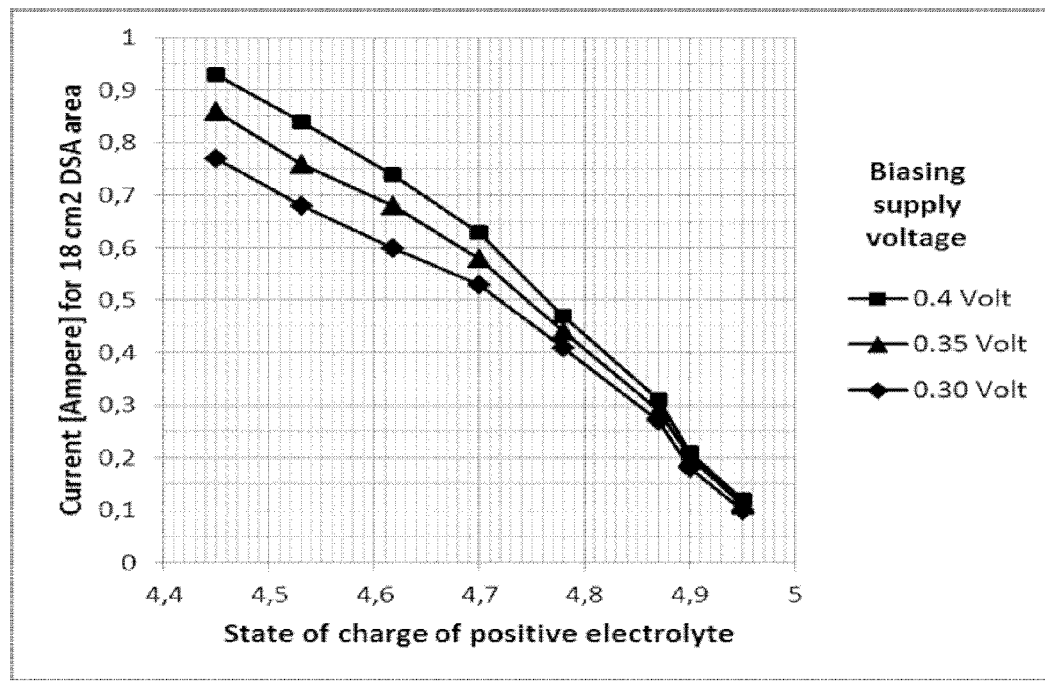
FIG. 6 shows the correlation characteristics curves in the Cartesian plane of the current measured at the indicated three different bias voltages applied to the test cell and the OCV voltage of a battery cell at the correspondent known state of charge of the vanadium redox couple in the positively charged electrolyte solutions used for the tests.

FIG. 6 shows the correlation characteristics in a Cartesian plane of the current measured at the indicated three different bias voltages applied to the test cell and the OCV voltage of a battery cell at the correspondent known state of charge of the vanadium redox couple in the positively charged electrolyte solutions used.

Figure 7:
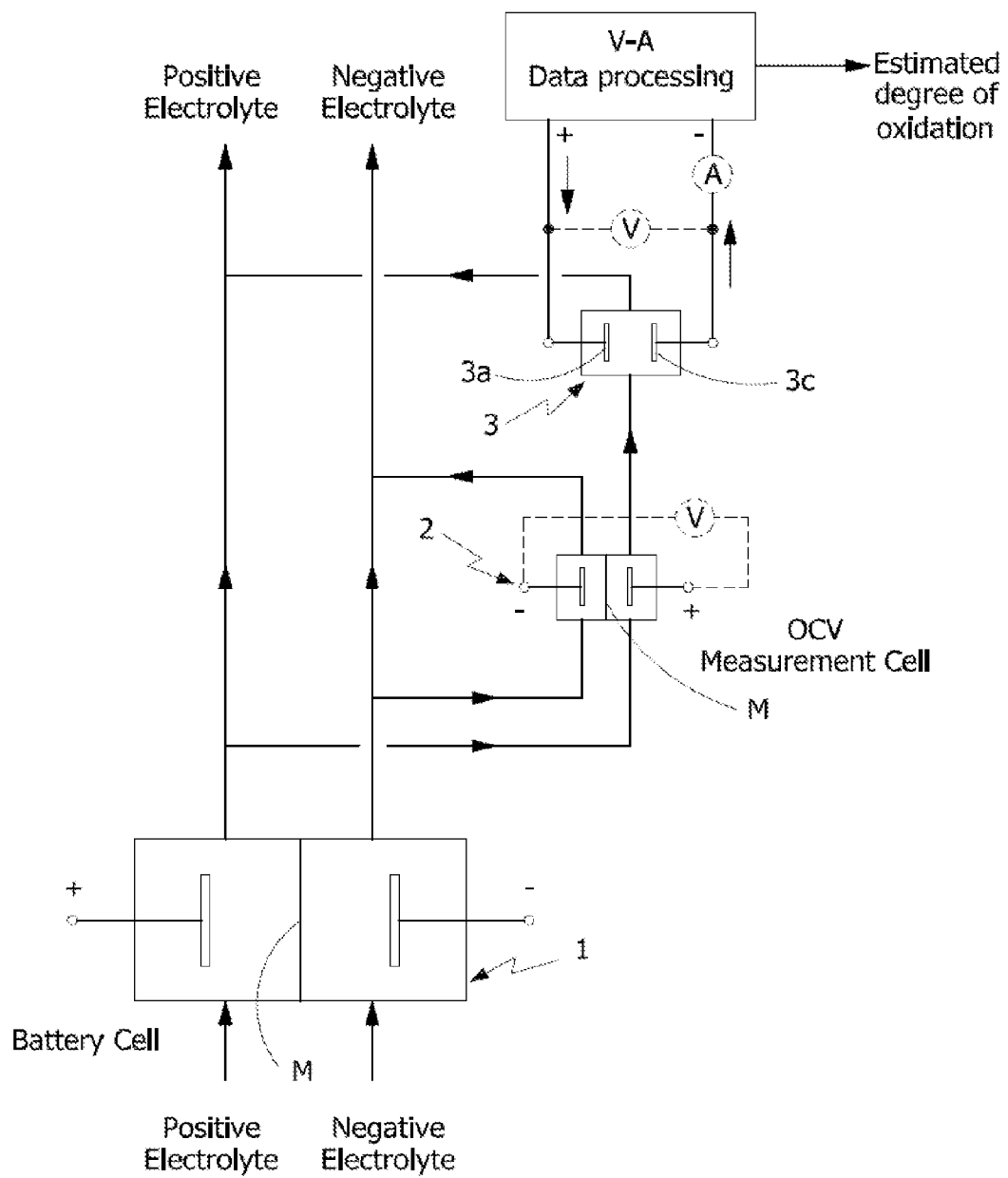
FIG. 7 illustrates an example of how the method of this disclosure may be implemented in a common RFB system, only partially and schematically traced in the drawing.

FIG. 7 illustrates an example of how the method of this disclosure may be implemented in a common RFB system, only partially and schematically traced in the drawing as a symbolic battery cell 1 the flow (electrode) compartments of which are traversed by the two streaming solutions, namely: the positive electrolyte and the negative electrolyte, respectively.

According to a common practice, the OCV of the battery cell is commonly monitored on a minuscule scaled replica 2 of the battery cell, through the flow compartments of which proportionate streams of the circulating electrolyte solutions are diverted. A voltmeter provides an instantaneous measure that assuming perfect balanced electrolyte solutions should correspond to respective states of charge of the two electrolyte solutions.

The method of this disclosure for estimating the degree of oxidation or state of charge of the sole positive electrolyte solution may be implemented, as depicted in the figure, by passing a stream of it through a stable electro catalytic positive metal electrode 3a and a negative porous carbon counter-electrode 3c constituting a undivided test cell 3, i.e. without any fluid impervious membrane permeable to ions, namely a permionic membrane M as it is the case with the battery and OCV cells 1 and 2, respectively.

The test cell 3 may have an enclosure, as schematically shown in the example depicted, for flowing there through the positive electrolyte solution, or a two electrode assembly comprising an outer positive metal electrode having an open structure readily flown through by the solution; for example an expanded metal sheet or wire mesh surrounding the porous carbon counter-electrode, insulated from one another by a fluid pervious plastic separator, adapted to be introduced inside a flow conduit of the circulating solution, or immersed in a pool of the circulating solution.

Suitable leads or equivalent means of electrical connections allows to connect the two electrodes to the positive output terminal and negative output terminal of a DC source 4 capable of delivering a current of up to one or more amperes though the test cell 3, at the bias conditions of the test cell 3 of selected output voltages that are substantially held constant by a regulating loop of the DC source 4, for the time necessary to read simultaneously the electrical current absorbed by the test cell 3 at the selected bias condition. Voltage-current measurements being performed according to the method of this disclosure are indicated in the block diagram of FIG. 7 by the respective instrument symbols V and A.

Preferably, output voltage and current measurements should be made without using a sense resistor in series to the test cell in order to avoid corrections of the voltage bias applied to the test cell.

Most preferably, the programmed output voltage and the measure of the current drawn by the test cell at the constant voltage bias are both extracted as analog signals from the DC source circuitry with commonly known circuital techniques. In particular, the output voltage signal may be drawn from a common resistive voltage divider of the output voltage that constitutes the feedback network of the control loop of a linear voltage regulator that control an output pass transistor. A signal representing the output current may be drawn starting from a commonly controlled scaled replica of the output pass transistor, the scaled current generated by which may be mirrored with the output current and thence a voltage signal proportional to the output current may be drawn from the output branch of a second mirror.

Of course, a specifically designed circuitry for electrically biasing the cell sensor 3 at a desired supply voltage and for simultaneously sensing the current absorbed by the sensor, may be used also for preliminarily generate a look up table of correlation of the response of the sensor to a plurality of calibration solutions of known degree of oxidation or state of charge.

A circuital embodiment of the DC source 4 and of the voltage and current measurement implements, allows the realization of an electronic system capable of managing the powering of the test cell, the collection and temporary storage of voltage-current data pairs and the production of a real-time estimated value of the degree of oxidation or state of charge of a positive electrolyte solution containing a V+4/V+5 redox ion couple of a working redox flow battery cell, as described herein below.

Figure 8:
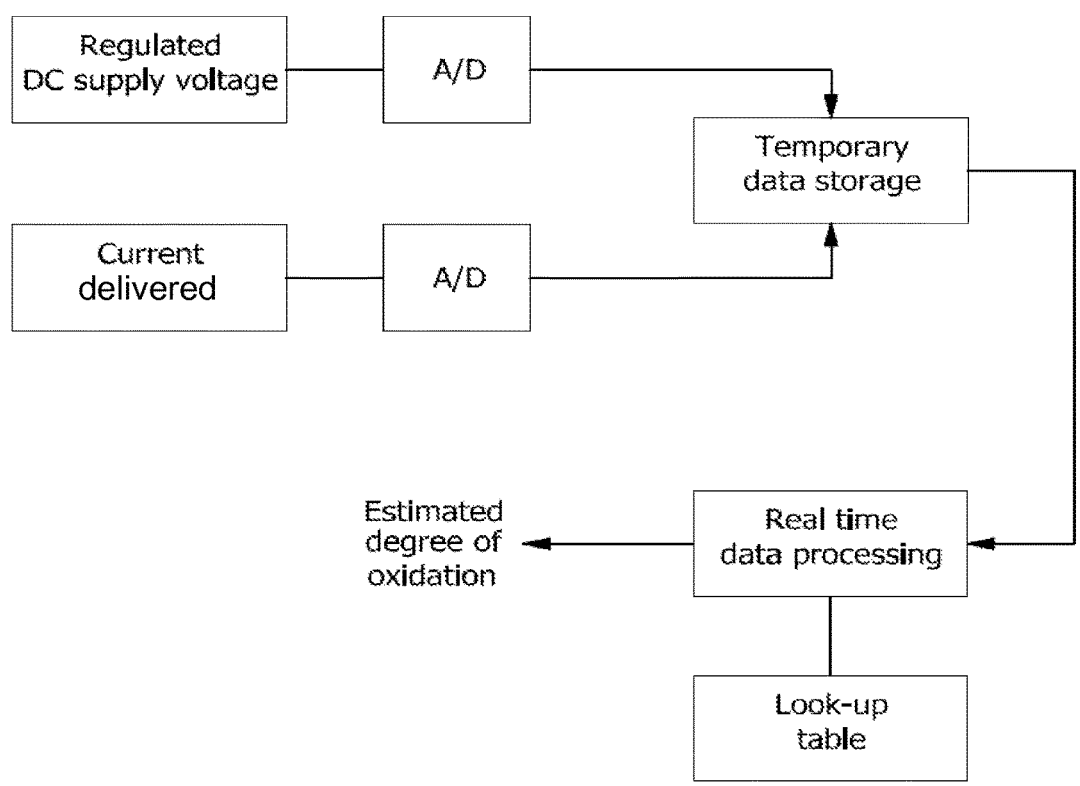
FIG. 8 is a basic block diagram of an exemplary embodiment of a system for real time generation of an estimated degree of oxidation of the redox ion couple of a positive electrolyte solution circulating in a working RFB system, according to an embodiment of the method of this disclosure.

As schematically illustrated in a basic exemplary block diagram of FIG. 8, properly scaled and buffered analog voltage signals representing the regulated output voltage of the power supply biasing the undivided cell sensor and the current absorbed by the sensor, respectively, may be sampled at clock beats and converted by common A/D converters into digital data pairs that may be stored in a work memory, for example a RAM.

A digital processor correlates every data pair read from the work memory to the correspondent degree of oxidation and/or to the correspondent state of charge of the redox ion couple contained in the positive electrolyte solution flowing in the battery cells, recorded in a look up table when calibrating the undivided cell sensor.

The generated estimated data may be compared with one or more threshold values for eventually alerting the operator of the risk of approaching a potentially dangerous high degree of oxidation of the redox couple.

Data processing capabilities of modern digital processors allows real time execution of computational algorithms over a plurality of sequential voltage-current data pairs read from the RAM, for making more robust, precise and reliable the identification of the point on the voltage-current plane of the response to the actual degree of oxidation or state of charge of the streaming solution provided by the biased cell sensor. A pre-filtering of disturbances by a sample data correlation algorithm, may be performed in order to filter out odd data pairs that may be accidentally acquired by the monitoring system.

By processing the real time produced estimated degree of oxidation or state of charge of the positive electrolyte solution and the normally monitored OCV it is possible to indirectly estimate by subtraction the state of charge of the negative electrolyte solution and thence the degree of unbalance that may have been cumulated in running the RFB system for a long period or after many charge-discharge cycles. The availability of this information in real time fashion is an attendant important result that is made possible by the method of this disclosure.

The various embodiments described above can be combined to provide further embodiments. Other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

[1]. Review of "*Redox flow cells for energy conversion*", C. Ponce de Leon, A. Frias-Ferrer, J. Gonzalez-Garcia, D. A. Szanto, F. C. Walsh, Elsevier, Journal of Power Sources 160 (2006), pages: 716-732;

[2]. "*Novel vanadium chloride/polyhalide redox flow battery*", Maria Skyllas-Kazacos, Elsevier, Journal of Power Sources 124 (2003), pages: 299-302;

[3]. "*A study of the Ce(III)/Ce(IV) redox couple for redox flow battery application*", B. Fang, S. Iwasa, Y. Wei, T. Arai, M. Kumagai, Elsevier, Electrochimica Acta 47 (2002), pages 3971-3976;

[4]. "*Chromium redox couples for application to redox flow batteries*", C.-H. Bae, E. P. L. Roberts, R. A. W. Dryfe, Pergamon, Electrochimica Acta 48 (2002), pages: 279-287;

[5]. "*Redox potentials and kinetics of the Ce3p/Ce4p, redox reaction and solubility of cerium sulphates in sulphuric acid solutions*", A. Paulenovaa, S. E. Creagerb, J. D. Navratila, Y. Weic, Elsevier, Journal of Power Sources 109 (2002), pages: 431-438;

[6]. "*A novel flow batte—A lead acid battery based on an electrolyte with soluble lead(II)IV. The influence of additives*", Ahmed Hazza, Derek Pletcher, Richard Wills, Elsevier, Article in Press, Journal of Power Sources xxx (2005) xxx-xxx;

[7]. "*A novel flow batte—A lead acid battery based on an electrolyte with soluble lead(II) III. The influence of conditions on battery performance*", Elsevier, Journal of Power Sources 149 (2005) 96-102.

[8]. "*State of charge monitoring methods for vanadium redox flow battery control*", Maria Skyllas-Kazacos, Michael Kazacos, Journal of Power Sources 296 (2011) 8822-8827.

The invention claimed is:

1. A method of instrumental assessment of the degree of oxidation or state of charge of a positive electrolyte solution containing a $V^{+4}/V^{+5}$ redox ion couple of a working redox flow battery cell, comprising:
   a) immersing a battery cell assembly comprising a stable electro-catalytic metal electrode and a porous carbon counter-electrode in the positive electrolyte circulating in a positive electrolyte solution flow compartment of the battery cell;
   b) supplying the two electrodes of the battery cell a positive regulated DC voltage between said stable electro-catalytic metal electrode and said porous carbon counter-electrode and measuring the current flowing through the battery cell at one or several different regulated DC supply voltages in a range comprising the interval from +0.35V to +0.45 V; and
   c) producing an estimated value of the degree of oxidation or state of charge of the positive electrolyte solution from at least a pair of measured voltage and current values within the region on a Cartesian voltage-current plane defined by said voltage interval.

2. The method of claim 1, wherein said estimated value is produced in real time fashion by correlating one or more instantaneous pairs of measured voltage and current values to a correspondent degree of oxidation or state of charge of the solution that is eventually read from a look-up table compiled by calibrating the response of said undivided cell on different positive electrolyte solutions of known degree of oxidation or state of charge.

3. The method of claim 2, wherein said correlation is carried out utilizing a plurality of voltage-current data pairs sequentially acquired at a plurality of different voltages applied to the cell electrodes.

4. The method of claim 2, further comprising a pre-filtering of disturbances by a sample data correlation algorithm.

5. A monitoring apparatus for producing a real-time estimated value of the degree of oxidation or state of charge of a positive electrolyte solution containing a V+4/V+5 redox ion couple of a working redox flow battery cell, comprising:
   a) a battery cell assembly comprising a stable electro-catalytic metal electrode and a porous carbon base counter-electrode to be immersed in the positive electrolyte solution;
   b) a DC power supply at programmable regulated DC output voltages for positively biasing said stable electro-catalytic metal electrode at one or several different regulated DC supply voltages in a range comprising the interval from +0.35V to +0.45V with respect to said porous carbon counter-electrode;
   c) current sensing means for sensing the current flowing through said battery cell at the regulated biasing supply voltage or voltages applied to said electrodes;
   d) analog/digital signal conversion means for converting analog sampled current sensed by said current sensing means and analog sampled biasing voltage into digital data pairs of correspondent current and voltage values;
   e) temporary data storage means for said digital data pairs of correspondent current and voltage values; and
   f) a look-up table of correlation of one or of a sequence of said paired values read from said temporary data storage means to the sought value of the degree of oxidation and/or or state of charge of the positive electrolyte solution.

6. The monitoring apparatus of claim 5, wherein said stable electro-catalytic metal electrode is an expanded sheet or wire mesh of titanium coated with oxides of metals selected from the group consisting of tantalum, tin, zirconium, hafnium, iridium and rhodium.

7. The monitoring apparatus of claim 5, wherein said porous carbon counter-electrode is a porous bed of carbon particles or fibers electrically in contact with a carbon or graphite current distributor.

8. The monitoring apparatus of claim 5, wherein said porous carbon counter-electrode is a porous bed of granules of active carbon elastically held against the surface of at least a carbon or graphite back plate connected to a negative output of said regulated DC supply.

* * * * *